(12) United States Patent
Henderson (10) Patent No.: US 9,801,937 B1
(45) Date of Patent: Oct. 31, 2017

(54) METHOD FOR TARGETING ANTIGENS UNIQUE TO A TUMOR

(71) Applicant: Dartmouth-Hitchcock Clinic, Lebanon, NH (US)

(72) Inventor: Eric R. Henderson, Lebanon, NH (US)

(73) Assignee: Dartmouth-Hitchcock Clinic, Lebanon, NH (US)

( * ) Notice: Subject to any disclaimer, the term of this patent is extended or adjusted under 35 U.S.C. 154(b) by 0 days.

(21) Appl. No.: 14/813,073

(22) Filed: Jul. 29, 2015

Related U.S. Application Data (60) Provisional application No. 62/030,412, filed on Jul. 29, 2014.

(51) Int. Cl.
| | | |
|---|---|---|
| *A61K 39/39* | (2006.01) | |
| *A61K 39/395* | (2006.01) | |
| *A61K 39/40* | (2006.01) | |
| *A61K 51/10* | (2006.01) | |
| *A61K 47/48* | (2006.01) | |
| *A61K 39/00* | (2006.01) | |

(52) U.S. Cl.
CPC ........ *A61K 39/39558* (2013.01); *A61K 39/40* (2013.01); *A61K 47/48446* (2013.01); *A61K 47/48484* (2013.01); *A61K 47/48507* (2013.01); *A61K 51/1009* (2013.01); *A61K 2039/507* (2013.01)

(58) Field of Classification Search
None
See application file for complete search history.

(56) References Cited

PUBLICATIONS

Paganelli, et al., "Three-Step Monoclonal Antibody Tumor Targeting in Carcinoembryonic Antigen-Positive Patients", "Cancer Research", Nov. 1, 1991, pp. 5960-5966, vol. 51, Publisher: American Association for Cancer Research, Published in: US.

*Primary Examiner* — Brad Duffy
*Assistant Examiner* — Nelson B Moseley, II
(74) *Attorney, Agent, or Firm* — Loginov & Associates; William A. Loginov (57) ABSTRACT

A method and system for targeting antigens unique to a tumor site. The method can include a first phase of monoclonal antibodies that bind to the tumor site. A second phase of monoclonal antibodies can be administered that bind to the first phase. A third phase of monoclonal antibodies can be administered that bind to the second phase. The third phase can include radionuclides to allow the tumor site to be imaged. Once identified, a phase of toxins can be administered, resulting in death of the tumor cells.

11 Claims, 8 Drawing Sheets

METHOD FOR TARGETING ANTIGENS UNIQUE TO A TUMOR

RELATED APPLICATIONS

This application claims the benefit of U.S. Provisional Patent Application Ser. No. 62/030,412, filed on Jul. 29, 2014, entitled METHOD FOR TARGETING ANTIGENS UNIQUE TO A TUMOR, which is expressly incorporated herein by reference.

FIELD OF THE INVENTION

The present disclosure relates to therapy for targeting antigens unique to a tumor, and more particularly to therapies using multiphase monoclonal antibody therapy.

BACKGROUND OF THE INVENTION

Cancer is predicted to become the leading cause of death in the United States in the next twenty years. As cases of cancer increase, medical experts are increasingly searching for effective treatments for each individual type of cancer. Treatments of the past included chemotherapy, which is generally an untargetered therapy that can be as harmful to cancerous cells as it is to healthy cells. Monoclonal antibodies (MABs) are a biological technology that allow for rapid creation and manufacture of proteins (antibodies) with receptors that bind to specific targets (antigens). However, current MAB therapies are only available in particular circumstances and in certain cancers, where the cancer presents particular known antigens.

SUMMARY OF THE INVENTION

This invention overcomes disadvantages of the prior art by providing a method for targeting antigens unique to a tumor and thereby providing a more direct and effective treatment for certain types of cancer. One aspect of the disclosure a method of administering multi-phase monoclonal antibody (MAB) therapy to a human patient, comprising: identifying a plurality of antigens present in a tumor site of a human patient; administering a first plurality of monoclonal antibodies (MABs), the first plurality of monoclonal antibodies comprising a first MAB corresponding to a first antigen of the first plurality of antigens and a second MAB corresponding to a second MAB of the first plurality of antigens; administering a second plurality of MABs, each of the second plurality of MABs corresponding to both the first MAB and the second MAB and having an identifier site corresponding to a unique antigen not native in the human body; and administering a third plurality of MABs, each of the third plurality of MABs corresponding to the unique antigen.

In one example, the method can include performing a biopsy of the tumor site.

In one example, the method can include identifying the plurality of antigens comprises performing a DNA microarray.

In one example, the first MAB and second MAB are administered in a dosage inversely proportional to the presence of antigens at the tumor site.

In one example, the first MAB comprises a binding site that binds to the first antigen and the second MAB comprises a binding site that binds to the second antigen.

In one example, the first MAB comprises an identifier site having an antigen that corresponds to the first antigen and the second MAB comprises an identifier site having an antigen that corresponds to the second antigen.

In one example, each of the second plurality of MABs comprises a first binding site corresponding to the first antigen and a second binding site corresponding to the second antigen.

In one example, the unique antigen comprises an antigen synthesized in a laboratory.

In one example, each of the third plurality of MABs comprises a first identifier corresponding to a second unique antigen and a second identifier comprising a radionuclide.

In one example, the second unique antigen is distinct from the first unique antigen.

In one example, the method can include imaging the tumor site to mark the tumor site using the radionuclides; and administering a toxin that binds to the first identifier of the third plurality of MABs.

Another aspect of the disclosure provides a system for administering multi-phase monoclonal antibody (MAB) therapy to a human patient, comprising: a first plurality of monoclonal antibodies (MABs), the first plurality of monoclonal antibodies comprising a first MAB corresponding to a first of a plurality of antigens identified at a tumor site and a second MAB corresponding to a second of the plurality of antigens identified at the tumor site; a second plurality of MABs, each of the second plurality of MABs corresponding to both the first MAB and the second MAB and having an identifier site corresponding to a unique antigen not found in the human body; and a third plurality of MABs, each of the third plurality of MABs corresponding to the unique antigen.

BRIEF DESCRIPTION OF THE DRAWINGS

The invention description below refers to the accompanying drawings, of which.

DETAILED DESCRIPTION

Figure 1:
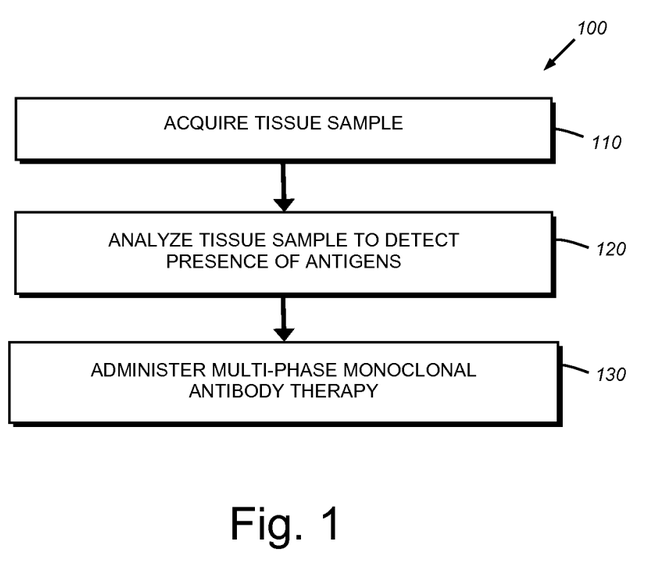
FIG. 1 is a flow chart depicting a method for targeting antigens unique to a tumor site according to one or more aspects of the disclosure.

FIG. 1 is a flow chart depicting a method 100 for targeting antigens unique to a tumor site according to one or more aspects of the disclosure.

At block 110, a tissue sample of the suspected tumor site is acquired. This may be done according to any number of methods. For example, when the suspected tumor is a soft tissue sarcoma, such as a liposarcoma or rhabdomyosarcoma, a biopsy can be conducted to remove a sample of tissue from the suspected tumor site of the patient. The biopsy can be conducted according to any number of biopsy methods or protocols, such as fine needle aspiration (FNA) biopsy, core needle biopsy, or surgical biopsy (e.g., when the suspected tumor is surgically removed).

At block 120, the tissue sample is analyzed to detect the presence of one or more antigens. An antigen can be a protein that has some inherent uniqueness and can be used to identify the origin of its cellular carrier. The tissue samples can be subject to a DNA microarray for the purpose of detecting the presence of one or more antigens in the tissue sample. The DNA microarray can output a listing of antigens present in the analyzed sample, and describes the relative amounts of each. Again, in the example where the tumor is a soft tissue sarcoma, the presence of one or more antigens can be indicative of the soft tissue sarcoma. Such antigens can include, for example, smooth muscle actin, S100, desmin, myoglobin, vimentin, myogenin, myoD, smooth muscle myosin, synaptophysin, or tyrosinase. In other examples, the antigens can include CD (cluster of differentiation) antigens, such as CD20, a B cell marker.

At block 130, multi-phase monoclonal antibody (MAB) therapy is administered based on the detected antigens at block 120. The MAB therapy is discussed in greater detail below with respect to FIGS. 2A-E and 3, which are schematic diagrams of a tumor site inside a human body depicting stages of administering multi-phase monoclonal antibody therapy according to one or more aspects of the disclosure.

Figure 2A:
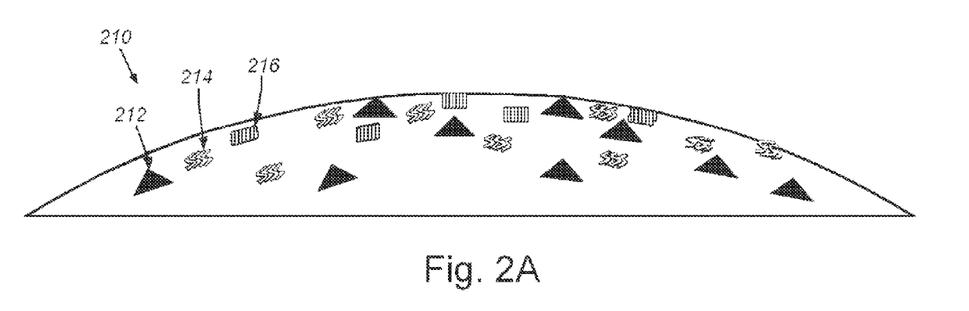
FIGS. 2A-E are diagrams of a method for administering multi-phase monoclonal antibody therapy according to one or more aspects of the disclosure.

FIG. 2A depicts a diagram of a tumor site 210 before administering multi-phase monoclonal antibody therapy. As shown in the diagram, the tumor site 210 can include one or more antigens 212-216. The antigens 212-216 can be the antigens identified above as block 120. The antigens 212-216 are depicted as located on a surface of the tumor site 210, but the tumor site 210 can have antigens 212-216 dispersed through the mass/volume of the tumor site. Illustratively, the antigens 212-216 can be any type of antigens that can be present in a tumor, such as the antigens described above with respect to soft tissue sarcoma. For example, such antigens include smooth muscle actin, S100, desmin, myoglobin, vimentin, myogenin, myoD, smooth muscle myosin, synaptophysin, or tyrosinase. The antigens 212-216 can be any type of antigens found in a tumor, including cancerous or non-cancerous cells. The antigens 212-216 can be present in the tumor in any concentration with respect to a total size, mass, or volume of the tumor or with respect to other antigens. As described above, the analysis performed at step 120 provides an output of the antigens 212-216 present in tumor site 210, as well as their relative concentrations at the tumor site 210. While the tumor site 210 is depicted as having three antigens 212-216, the tumor site 210 can have any number of antigens present, such as one or more antigens. In one example, the tumor site 210 includes at least two specific antigens.

Figure 2B:
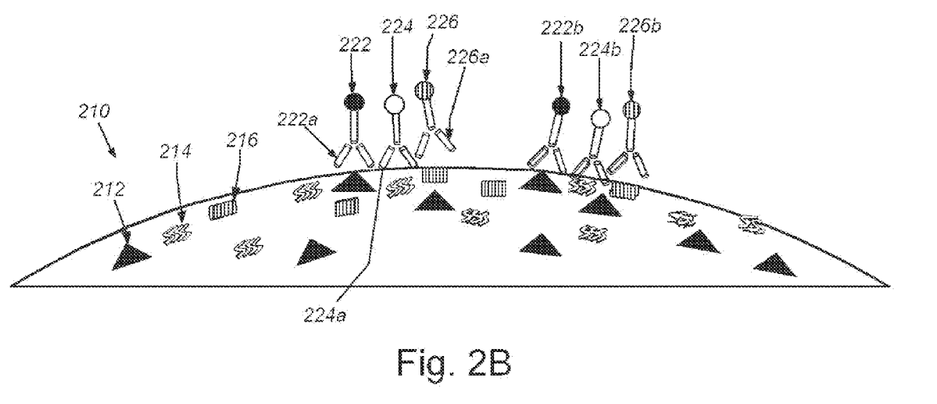

FIG. 2B depicts a diagram of the tumor site 210 after a first phase of MABs 222-226 have been administered to the patient. The MABSs 222-226 can be any type of MAB, such as murine MABs, chimeric, humanized, or human MABs. The MABs can be produced through the hybridoma method or could be produced a number of other methods. In one example, the MABs can be produced by immunizing a mouse, rat, or other mammal against a particular antigen. Such immunization causes the mammal to begin producing specific antibodies against the particular antigen. At this time, the spleen of the mammal can be removed. When PEG (polyethylene glycol) is added to the mixture, hybridomas can be formed. The fused hybridoma cells are then separated from the unfused B cells and myeloma cells. Once placed in HAT (hypoxanthine-aminopterin-thymidine) medium, only the fused cells survive. The fused hybridomas are then separated and individual cultured to form MABs.

The MABs can have any type of structure. In one example, the MABs can have one or more light chains and/or heavy chains. The light chains are sites at which the hypervariable regions, e.g., combing site, generally exist, and where binding to the target antigen can occur. The heavy chains are where a drug, toxin, or radionuclide can be attached.

As shown, the first phase includes a first MAB 222, a second MAB 224, and a third MAB 226. The first MAB includes a binding site, or receptor site, 222a. The binding site, or receptor site, 222a can also be referred to as the "hypervariable region" or the "antigen binding site." The binding site 222a corresponds to the antigen 212 such that the first MAB 222 will bind to the antigen 212 via the binding site 222a. In this regard, the receptor site 222a is constructed so that it should bind to the targeted antigen, and in some circumstances, only to the targeted antigen. The first MAB 222 also includes an identifier site 222b. The identifier site 222b corresponds to the antigen 212 such that the identifier site 222b includes antigen 212 material thereon. Put another way, the receptor site has an opposing electric charge from the antigen such that the binding site is the mirror image of the antigen with all charges and contours being inverted.

Similarly, the first phase of MABs can include a second MAB having a binding site 224a and a identifier site 224b corresponding to the second antigen 214, and a third MAB having a binding site 226a and an identifier site 226b corresponding to the third antigen. While the first phase of MAB therapy depicts three antigens and three MABs, two or more MABs may be administered to the human patient for binding to antigens at the tumor site. In a specific example, between two and six MABs can be administered during this phase of therapy.

The dosing of the first phase of MABs can be any dose considered effective for treatment, and can vary based on metabolism and/or bioavailability of the therapy. In one operational, therapeutic example, the dosing can be 375 mg/m$^2$, with an average adult having a surface area of 1.9 m$^2$, resulting in a dose of approximately 713 mg. The MABS 222-226 can each be provided in an identical dosage, or in another example the respective dosages among the MABS 222-226 can be different. In an embodiment, the dosages can be provided to be inversely proportional to the concentration of the corresponding antigen in the tumor site. That is, if a particular antigen is scarce at the tumor site, the corresponding MAB can be provided in a greater dosage to ensure binding between the MAB and the scarce antigen. Similarly, if a particular antigen is plentiful at the tumor site, the dosage can be decreased. The MABS 222-226 can be provided orally to a patient, intravenously, or through another equivalent delivery mechanism/modality.

Figure 2C:
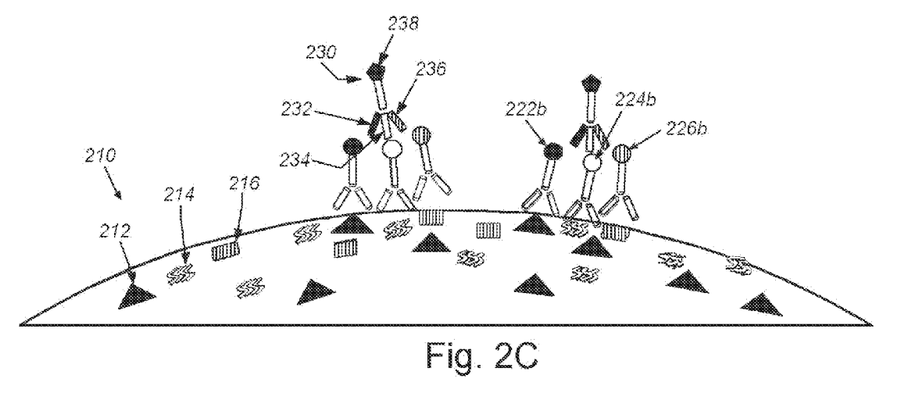

FIG. 2C depicts a diagram of a tumor after a second phase of MABSs 230 have been administered. As shown, each of the MABs 230 include a plurality of binding sites 232-236 that respectively correspond to the antigens 212-216 and the identifier sites 222b-226b. The dosing amount of MABs 230 can be any effective amount, and the MABs 230 can be delivered any time after the first phase of MABs 220.

During this phase, each of the MABs 230 can bind to each of the MABS 222-226 administered during the first phase. Specifically, binding site 232 of the MAB 230 can bind to the identifier site 222b, binding site 234 can bind to the identifier site 224b, and binding site 236 can bind to the identifier site 226b. Thus, a single MAB 230 can bind to a plurality of MABs 220 from the first phase of therapy. As described above, while three antigens 212-216 are depicted, its is contemplated in an alternate implementation that two or more antigens can be targeted at the tumor site. In the example of two antigens, the MABs 230 include two binding sites.

The MABs 230 include an identifier site 238. The identifier site 238 can include a first unique antigen that is not native to the human body, e.g., not naturally found, nor naturally occurring within the human body. In this regard, the first unique antigen of the identifier site 238 can be developed in a laboratory setting. The unique antigen can be a copy of a unique protein found in a non-human species. One example of this would be the *Helicobacter pylori* Stool Antigen (HpSAg). *Helicobacter pylori* is a well-studied bacterium and HpSAg is a protein which is unique to this species. HpSAg can be manufactured in the laboratory setting using polymerase chain reaction (PCR) technology combined with RNA polymerase and ribosomal activation. For larger-scale production, such as with synthetic human insulin, bacteria or yeast cells are implanted with the desired protein's concordant RNA strand and then cloned, allowing mass production of the desired protein antigen.

Figure 2D:
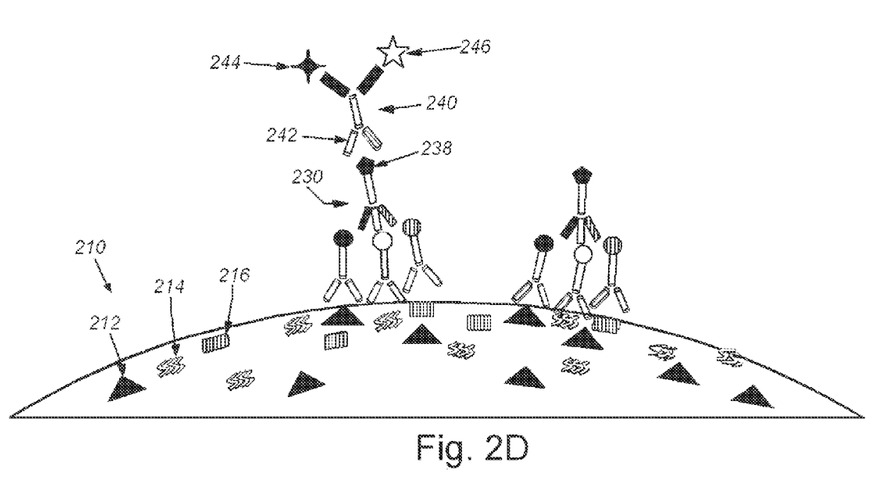

FIG. 2D depicts a diagram of a tumor after a third phrase of MABs 240 have been administered in accordance with an illustrative embodiment. As shown, each of the MABs 240 includes a binding site 242 that binds with the identifier 238. Since identifier 238 includes the first unique antigen, there is minimal-to-negligible risk that the MABs 240 will selectively/exclusively bind to areas remote from the tumor site 210. Accordingly, even if the antigens 212-216 are naturally occurring in the body, the MABs 240 will only bind to a tumor site with the particular antigen makeup identified at block 120 and matching the antigen binding sites 222a-226a. This is unless, of course, the tumor site 210 is only of many tumor sites throughout the body with a similar antigen makeup.

Illustratively, the MABs 240 can each include a pair of identifier sites 244 and 246. The identifier site 244 includes a second unique antigen that is not native to the human body, e.g., not naturally found/occurring in the human body. In this regard, the second unique antigen can be a laboratory-produced antigen. In one example, the second unique antigen is a different antigen from the first unique antigen provided at identifier site 238. The identifier site 246 can illustratively include a radionuclide that can be imaged from outside the body.

After the third phase, the radionuclides 246 can be imaged from outside the body (e.g., MRI, CT, PET, or any other imaging technique/modality) to identify the tumor site 210 in the patient, and to identify the overall shape, size, and location of the tumor site within the patient. During imaging, it can be verified that the third phase of MABs binded to the correct tumor site and did not instead bind to a region of healthy tissue inside the patient. If additional radionuclides 246 are identified away from the tumor site 210 during imaging, this could mean there are additional tumor sites distant from the tumor site 210 within the body that have the same antigen markers as the tumor site 210. These additional tumor sites can then be subjected to biopsy to confirm.

Figure 2E:
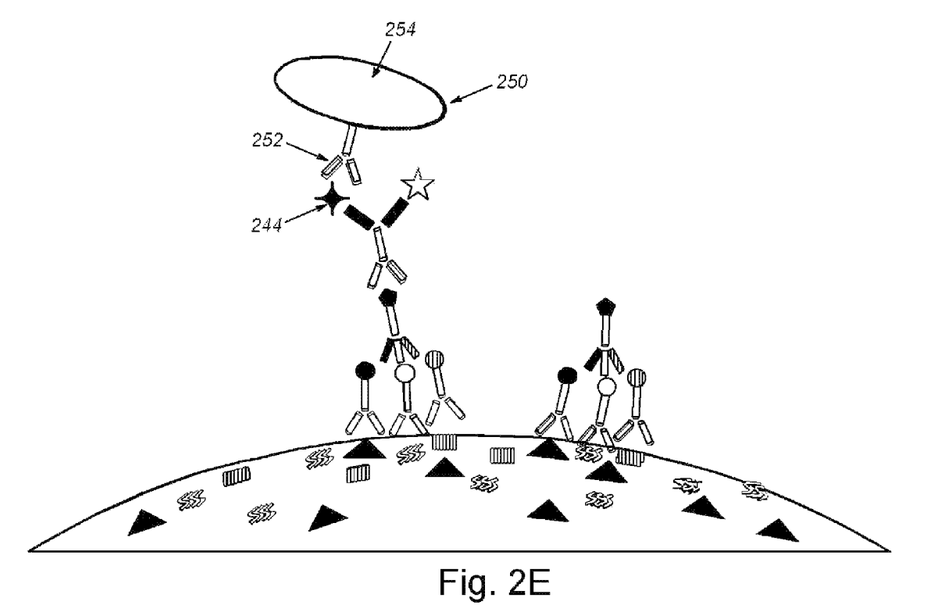

FIG. 2E depicts a diagram of a tumor site after a toxin 250 is administered.

Once the tumor site 210 is identified is being marked by the radionuclides, a toxin MAB 250 can be administered. During this phase, the toxin MAB 250 includes a binding site 252 that binds to the identifier 244. The toxin MAB 250 includes a toxin 254 that can be administered to the tumor site 210. Once the toxin MAB 250 binds to the identifier site 244, the toxin 254 can be delivered to the tumor site 210.

Since identifier 244 includes the second unique antigen, there is little to no risk that the toxin MABs 250 will bind to areas distant from the tumor site 210. In this regard, even if the antigens 212-216 are naturally occurring in the body, the toxin MABs 250 will only bind to a tumor site with the particular antigen makeup identified at block 120 and matching the antigen binding sites 222a-226a. This is unless, of course, the tumor site 210 is only of many tumor sites throughout the body with a similar antigen makeup.

The toxin 254 can be any type of toxin that can inhibit the growth of or cause the death of cells at the tumor site 210. In one example, the toxin can include ricin, diphtheria toxin, *pseudomonas* exotoxin, deglycosylated A chain.

Figure 3:
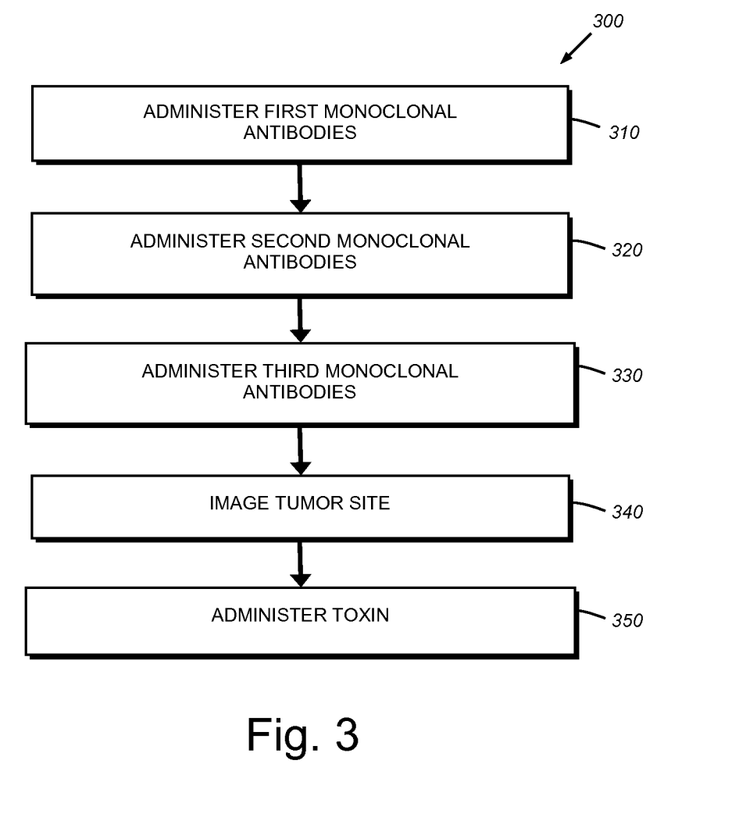
FIG. 3 is a flow chart depicting a method for administering multi-phase monoclonal antibody therapy according to one or more aspects of the disclosure.

FIG. 3 is a flow chart depicting a method for administering multi-phase monoclonal antibody therapy according to one or more aspects of the disclosure.

At block 310, a first phase of MABs can be administered. In this regard, the first phase of MABs can be the first phase described above with respect to first phase 222-226. The first phase can be administered by any method, such as orally, intraveneously, etc., and can be administered according to any dosage.

At block 320, a second phase of MABs can be administered. The second phase of MABs can be the second phase described above with respect to second phase 230. The second phase of MABs can bind to the first phase of MABs administered at block 310. The second phase can be administered by any method, such as orally, intraveneously, etc., and can be administered according to any dosage. The second phase can be administered any time after the first phase.

At block 330, a third phase of MABs can be administered. The third phase of MABs can be the third phase described above with respect to third phase 240. The third phase of MABs can bind to the second phase of MABs administered at block 320. The third phase can be administered by any method, such as orally, intraveneously, etc., and can be administered according to any dosage. The third phase can be administered any time after the second phase.

At block 340, imaging can be taken of the tumor site. In this regard, the third phase of MABs can include radionuclides, or any other type of particles, substance, or material capable of being imaged from outside the body. The imaging can verify the location of the tumor, and can confirm the size and shape of the tumor. The imaging can also confirm that any of the first through third phases of MABs did not bind to incorrect binding sites. The imaging process can occur any time after the third phase is administered at block 340.

At block 350, a toxin can be administered. The toxin can be the toxin described above with respect to toxin MAB 250. The toxin can bind to the third phase of MABs and can administer a toxic substance to the tumor site, thereby causing death of the tumor cells and elimination of the tumor within the body. The toxin can be administered by any method, such as orally, intraveneously, etc., and can be administered according to any dosage. In one example, block 340 is optional and block 350 can take place immediately after the third phase is administered at block 330.

Figure 4:
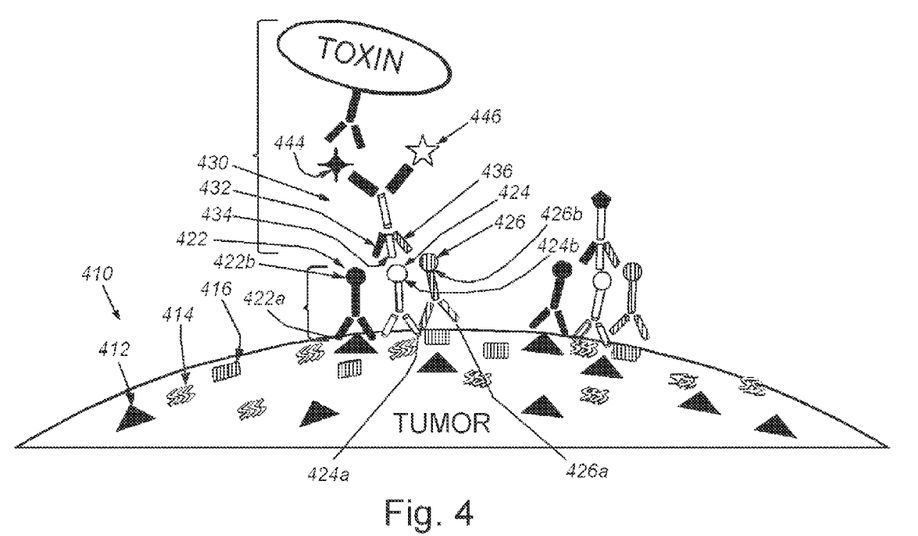
FIG. 4 depicts a diagram of a method for administering multi-phase monoclonal antibody therapy according to another aspect of the disclosure

FIG. 4 depicts a diagram of a method for administering multi-phase monoclonal antibody therapy according to another aspect of the disclosure. In this example, the second phase and third phase referred to above with respect to FIGS. 2A-2F can be combined into a single phase. In particular, a first MAB phase can be provided that is identical to the first phase described above in FIG. 2B.

The first phase administered to the tumor site 410 includes a first MAB 422, a second MAB 424, and a third MAB 426, which can be similar to the MABs 222-226 described above. The first MAB 422 includes a binding site, or receptor site, 422a, similar to binding site 222a described above. The binding site 422a corresponds to the antigen 412, which can be similar to antigen 212 described above, such that the first MAB 422 will bind to the antigen 412 via the binding site 422a. The first MAB 422 also includes an identifier site 422b, similar to site 222b described above.

Similarly, the first phase of MABs can include a second MAB 424 having a binding site 424a and a identifier site 424b corresponding to the second antigen 414, and a third MAB having a binding site 426a and an identifier site 426b corresponding to the third antigen, similar to the second and third MABs 224 and 226 described above.

A second phase of MABSs 430 can be administered. As shown, each of the MABs 430 include a plurality of binding sites 432-436 that correspond to the antigens 412-416 and the identifier sites 422b-426b. The dosing amount of MABs 430 can be any effective amount, and the MABs 430 can be delivered any time after the first phase of MABs 420.

During this phase, each of the MABs 430 can bind to each of the MABS 422-426 administered during the first phase. Specifically, binding site 432 of the MAB 430 can bind to the identifier site 422b, binding site 434 can bind to the identifier site 424b, and binding site 436 can bind to the identifier site 426b. Thus, a single MAB 430 can bind to a plurality of MABs 420 from the first phase of therapy. As described above, while three antigens 412-416 are depicted, it is contemplated in an alternate implementation that two or more antigens can be targeted at the tumor site. In the example of two antigens, the MABs 430 include two binding sites.

The second phase MABs 430 can each include a pair of identifier sites 444 and 446. The identifier sites 444 and 446 can be similar to the identifier sites 244 and 246 described above. Imaging and/or toxin delivery can thus commence as described above.

It is further contemplated that the compounds as well as the method/procedure steps provided above can be part of a kit that is provided to a practitioner or researcher for the purpose of carrying out the techniques of the illustrative embodiments. The kit can include appropriate reagents, mixing and fluid-handling devices as well as detailed instructions for carrying out the method in written and/or electronic form (e.g. an address to a website that guides the user).

It should be clear that the above-described method and kit effectively target tumors in mammalian bodies in a manner that selectively destroys tumor cells while maintaining minimal deleterious effects on normal cells. This method and kit can be applied to a variety of tumor cell types and sites within the body.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments of the apparatus and method of the present invention, what has been described herein is merely illustrative of the application of the principles of the present invention. In general, this description describes a method/procedure, system and kit for performing the procedure on mammalian subjects. The method/procedure can be used for treatment, diagnostic and research on live specimens. Accordingly, this description is meant to be taken only by way of example, and not to otherwise limit the scope of this invention.

What is claimed is:

1. A method of administering multi-phase monoclonal antibody (MAB) therapy to a human patient, comprising:
   identifying a plurality of antigens present in a tumor site of a human patient;
   administering a first plurality of monoclonal antibodies (MABs), the first plurality of monoclonal antibodies comprising a first MAB configured to bind to a first antigen of the first plurality of antigens and a second MAB configured to bind to a second antigen of the first plurality of antigens;
   administering a second plurality of MABs, each of the second plurality of MABs configured to bind to both the first MAB and the second MAB and having an identifier site comprising a unique antigen not native in the human body; and
   administering a third plurality of MABs, each of the third plurality of MABs configured to bind to the unique antigen.

2. The method of claim 1, further comprising:
   performing a biopsy of the tumor site.

3. The method of claim 1, wherein identifying the plurality of antigens comprises performing a DNA microarray.

4. The method of claim 1, wherein the first MAB and second MAB are administered in a dosage inversely proportional to the presence of antigens at the tumor site.

5. The method of claim 1, wherein the first MAB comprises a binding site that binds to the first antigen and the second MAB comprises a binding site that binds to the second antigen.

6. The method of claim 5, wherein the first MAB comprises an identifier site comprising the first antigen and the second MAB comprises an identifier site comprising the second antigen.

7. The method of claim 6, wherein each of the second plurality of MABs comprises a first binding site configured to bind to the first antigen and a second binding site configured to bind to the second antigen.

8. The method of claim 1, wherein the unique antigen comprises an antigen synthesized in a laboratory.

9. The method of claim 1, wherein each of the third plurality of MABs comprises a first identifier comprising a second unique antigen and a second identifier comprising a radionuclide.

10. The method of claim 9, wherein the second unique antigen is distinct from the first unique antigen.

11. The method of claim 9, further comprising:
    imaging the tumor site to mark the tumor site using the radionuclides; and
    administering a toxin that binds to the first identifier of the third plurality of MABs.

* * * * *